United States Patent [19]
Corbucci

[11] Patent Number: 5,645,570
[45] Date of Patent: Jul. 8, 1997

[54] METHOD AND DEVICE FOR MONITORING AND DETECTING SYMPATHO-VAGAL ACTIVITY AND FOR PROVIDING THERAPY IN RESPONSE THERETO

[75] Inventor: Giorgio Corbucci, San Giovanni In Persiceto, Italy

[73] Assignee: Sorin Biomedica S.p.A., Vercelli, Italy

[21] Appl. No.: 261,497

[22] Filed: Jun. 17, 1994

Related U.S. Application Data

[63] Continuation of Ser. No. 36,934, Mar. 25, 1993, abandoned.

[30] Foreign Application Priority Data

Mar. 26, 1992 [IT] Italy ................... TO92A0268

[51] Int. Cl.⁶ ..................................... A61N 1/39
[52] U.S. Cl. ................................................ 607/5
[58] Field of Search ................. 128/697; 607/4, 607/5

[56] References Cited

U.S. PATENT DOCUMENTS

| | | |
|---|---|---|
| 3,658,055 | 4/1972 | Abe et al. . |
| 3,699,949 | 10/1972 | O'Hanlon, Jr. et al. . |
| 3,837,333 | 9/1974 | Bruckheim . |
| 4,248,244 | 2/1981 | Charnitski et al. . |
| 4,796,620 | 1/1989 | Impan ............... 607/5 |
| 4,830,006 | 5/1989 | Haluska et al. ............ 607/4 |
| 5,058,599 | 10/1991 | Andersen . |
| 5,086,772 | 2/1992 | Larnard .................. 607/4 |
| 5,193,550 | 3/1993 | Duffin . |
| 5,330,507 | 7/1994 | Schwartz .............. 128/697 |

FOREIGN PATENT DOCUMENTS

| | | |
|---|---|---|
| 183351 | 6/1986 | European Pat. Off. . |
| 348271 | 12/1989 | European Pat. Off. . |
| 86/05698 | 9/1986 | WIPO . |

OTHER PUBLICATIONS

Biomedizinische Technik, vol. 34, No. 7/8, 1 Jul., 1989 –1 Aug. 1989, Berlin, DE, pp. 177–184, Schaldach: "Pep–Gesteuerter herzschrittmacher".

*Primary Examiner*—William E. Kamm
*Attorney, Agent, or Firm*—Popovich & Wiles, P.A.

[57] ABSTRACT

A device for controlling therapeutic means acting on a patient comprises means for detecting the sympatho-vagal balance of the patient and processor means for generating a control signal for the therapeutic means combined in a circuit assembly which allows the device to be implanted in the body of said patient.

53 Claims, 2 Drawing Sheets

METHOD AND DEVICE FOR MONITORING AND DETECTING SYMPATHO-VAGAL ACTIVITY AND FOR PROVIDING THERAPY IN RESPONSE THERETO

This is a continuation of U.S. application Ser. No. 08/036,934, filed Mar. 25, 1993 now abandoned.

DESCRIPTION

FIELD OF THE INVENTION

The present invention is directed generally to the problem of providing means for producing updated information on the sympatho-vagal balance for the purpose of controlling a therapeutic sequence of pharmacological and/or electrical nature.

Currently the measurement or detection of the sympatho-vagal activity is performed for the most part by external instruments.

Introduction to the Physiological Aspects of the Problem

The heart performs a mechanical function modulated by the sympathetic and vagal nervous activity, with consequent variations in the cardiovascular and respiratory parameters. In particular, the sympathetic component generally has a stimulating effect, whilst the vagal component has a depressive effect on the cardiovascular and respiratory variables mentioned hereinabove. Moreover, the role of a predominant sympathetic action in the creation of arrhythmia and even as a potential primary cause of sudden cardiac arrest is widely reported in the literature.

On the other hand, serious bradycardiac syndrome and hypotension may correspond to a dominant vagal action so that an important element in the balance of the cardiovascular system may be identified as the correct balance of these two actions.

For example, it has been shown that the absence of the vagal component, or the equivalent predominance of the sympathetic component, in post-infarction patients is associated with a probability of death of 34% as against 9% of patients having a high vagal activity, both evaluated in the fourth year after the infarction (see the article "Decreased heart rate variability and its association with increased mortality after acute myocardial infarction" by Kleiger, Miller, Bigger, Moss - Am.J.Card. 1987; 59:256–262). In the same way, it is known that, although on the one hand excessive sympathetic activity is the element which makes the initiation of ventricular fibrillation easier, on the other hand, the defibrillation threshold falls significantly with an increase in the sympathetic activity. If one considers that there are various pharmacological possibilities (implantable pumps) or electrical possibilities (vagal stimulation or inhibition and sympathetic stimulation or inhibition, single and two-chamber cardiac stimulation and defibrillation) for controlling the components of sympatho-vagal activity, one understands the interest in a system which allows the continuous measurement of this latter with the consequent possibility of performing an effective therapeutic dotion.

DESCRIPTION OF THE PRIOR ART

Currently, the measurement of sympatho-vagal activity is carried out only with external instrumentation, by the following methods.

Valsalva Procedure

The patient performs a forced inhalation with open glottis through a rubber nozzle connected to a sphygmomanometer in such a way as to produce a pressure of 40 mm of Hg for 15 seconds. Subsequently the patient is invited to breath normally through the nose. An analysis of variations in the heart rate during this exercise makes it possible to evaluate a parameter, called the Valsalva Ratio or VR, defined as the ratio between the greatest R-R interval in the reflex bradycardiac phase consequent on the effort exerted, and the shortest R-R interval observed during the exertion of the effort. The exercise in question evaluates both the response of the orthosympathetic system and that of the parasympathetic system. Values of $VR \geq 1.4$ are considered normal.

Handgrip Test

The patient is invited to grip an arm brace of a sphygmomanometer in such a way as to generate a pressure of the order of 30% of the value of a maximum force. The parameters detected are the heart rate and diastolic arterial pressure, PAd, in three consecutive tests respectively in the first, second and third minutes of effort.

This method enables the effectiveness of the operation of the orthosympathetic system to be evaluated: PAd increments of at least 16 mm of Hg with respect to base values are considered physiological, whilst the heart rate must rise by at least 10% with respect to its base values.

Posturel Test

The patient is initially in a clinostatic position and is invited to move to the standing position in less than three seconds and then to remain there for three minutes. The method enables the calculation of two indices correlated, respectively, with the minimum heart rate before the movement from the clinostatic position to the standing position, with the maximum rate following achievement of the standing position, as well as the minimum rate reached after about 30 seconds in the standing position. This test evaluates simultaneously the operation of the orthosympathetic and parasympathetic systems.

Heatbeat/hearbeat Analysis

This test evaluates quantitatively the respiratory arrhythmia induced in the subject under test by his taking six deep breaths in one minute. Based on the heart rate trend recorded during the test, it derives the average of the variations in the heart rate between the maximum value, corresponding to the inhalation phase, and the minimum value, corresponding to the exhalation phase, for the six consecutive breaths taken. Normal values are greater than 15 bpm. The test is very useful for an evaluation of the operation of the parasympathetic system.

All four methods described up to now are explained, for example, in the volume "La valutazione strumentale della funzionalita del sistema nervoso vegetativo" di Cugnoli, Bongiovanni, De Grandis, Serra-Appunti di Elettromiografia Clinica, Verona, B i & Gi Editori, 1987 (authors: Arrigo, De Grandis, Serra).

Power Spectral Density

This method makes it possible to evaluate a sympatho-vagal balance index directly. The technique in question is based on a record taken over several minutes, typically 20, of spontaneous cardiac activity either extracted from a Holter recording, or taken directly from a patient under standard conditions such as, for example, controlled frequency respiration. The processing algorithm performs a spectral analysis on the trend signal of atachogram of the stored cardiac periods. Two spectral components are typically displayed: one of high frequency, for example 0.25 Hz, and one of low frequency, for example 0.1 Hz. The high-frequency component represents a quantitative evaluation of the respiratory arrhythmia and depends principally on the efferent vagal activity. The low frequency component is correlated to the so-called Mayer waves which represent fluctuations in the heart rate trend with a period of the order of 10 seconds; this component is however linked both to the vagal and to the sympathetic efferent activity. The sympatho-vagal balance index is the ratio between the low frequency and high frequency components. Reference may be made to the article "Power spectral analysis of heart rate variability and arterial pressure variabilities as a marker of sympatho-vagal interaction in man and conscious dog" by Pagani, Lombardi, Guzzetti, Rimoldi, Furlan, Pizzinelli, Sandrone, Malfatto, Dell'Orto, Piocaluga, Turiel, Baselli, Cerutti, Maliani-Circulation research 1986; 59: 178–193.

Standard Deviation of the R-R Intervals

This method is typically applicable to 24-hour Holter recordings. The sympatho-vagal balance is expressed quantitatively by means of the variability of the heart rate interpreted as the standard deviation of the R-R intervals from the average value evaluated in a predetermined time interval. In the case of a 24-hour Holter analysis, the time interval considered is typically one hour so that the standard deviation of the R-R intervals is provided hour by hour relative to the average value evaluated in the same time interval. An increase in the sympathetic activity (or a reduction in the regal activity) is typically associated with a seduction in the variability of the heart rate as defined above. In this respect see the article by Kleiger, Miller, Bigger, Moss mentioned above.

Method of Analysis of the Variability of the Heart Rate by Comparison of Consecutive Periods This method is also utilised typically for analysis of 24-hour Holter recordings. The sympatho-vagal balance is expressed by means of the variability of the heart rate expressed as the number of R-R intervals which, in a given time interval, differ from the preceding interval by at least a predetermined quantity. Typically the reference time interval is one hour and the discrimination threshold between two consecutive R-R intervals is 50 ms. Therefore, in this case, the number of R-R intervals which differ from the preceding interval by at least 50 ms is provided hour by hour. A high sympathetic activity or a depressed vagal activity causes a reduction in the variability of the heart rate defined as above. In particular, hourly values of the order of 200 when awake and 400 during sleep are considered normal. In this respect see the article "New method for assessing cardiac parasympathetic activity using 24 hour electrocardiograms" by Ewing, Neilson, Trevis in Br. Heart J. 1984; 52: 396–402.

It should also be stressed that this latter method has the advantage over the previous one of distinguishing the contribution of the vagal nervous system from that of the sympathetic system more markedly.

This is linked to the fact that considerable differences between consecutive R-R intervals, that is to say, a high variability expressed according to this latter method, is also seen as a high variability according to the preceding method, whilst the contrary is not always true.

These two methods are therefore not equivalent.

This fact is for example found in patients having significant variations in heart rate compared with the average value in the time interval under consideration, but With small variations, for example <50 ms, between consecutive R-R intervals: in this situation the standard deviation will be consistent whilst the variability related to variations between consecutive periods will be low.

As may be noted, all the methods described above lend themselves to being utilised only with the aid of significant external instrumentation and/or sophisticated calculation systems not compatible with the current technology for implantable devices, in effect making continuous monitoring of the sympatho-vagal balance, and consequent control of therapeutic action, impossible. In particular, the methods applied to the 24-hour Holter recordings exploit sophisticated algorithms for recognising arrythmia and anomalous heartbeats in general, in order to eliminate from the processing those parts of the electrocardiogram in which such events are present. In general it is a good rule to apply the analysis to specimens of the ECG with less than five extrasystoles per hour and this underlines the importance of the recognition of anomalous cardiac events.

OBJECTS AND SUMMARY OF THE INVENTION

The object of the present invention is to provide a device which is at least partially implantable so as to be able to measure sympatho-vagal activity in a continuous manner and with time constants such as to allow the possible piloting of a pharmacological and/or electrical therapeutic action, effected preferably by means of a separate implantable device connected to the first or integrated in the latter so as to form a single implantable assembly.

According to the present invention this object is achieved by a device having the characteristics set out specifically in the following claims.

In summary, the basic parameter which is utilised is the variability of the heart rate evaluated as the number of consecutive R-R intervals which differ from one another by at least a minimum threshold which is programmable and related to the programmed time interval.

From this point of view the invention is conceptually similar to the method of analysis of the variability by comparison of consecutive periods described hereinabove.

The solution of the invention is however distinguished from this known technique by the following characteristics.

i) The method of detection is based on timing rather than morphology.
ii) The method of detecting the electrocardiology signal is based on selective intracardiac sensing rather than on general surface electrodes.
iii) Continuity of the measurement and testing of the sympatho-vagal balance without the temporal limits imposed by the Molter analysis.
iv) The complete difference in technology between an external system and an implantable one is well known to those skilled in this particular field.

As previously mentioned, it is important to exclude anomalous cardiac events from the analysis of the variability of the R-R intervals.

Known methods which use Holter analysis succeed in recognising ventricular extrasystoles by means of complex algorithms for the morphological analysis of the recorded signal. This is possible thanks to the fact that the surface ECG depends morphologically on the sense and direction of propagation of the overall myocardiac depolarisation and subsequent repolarisation.

This morphology thus depends on the point at which the cellular depolarisation starts and on the direction of propagation followed, according to the well-known Einthoven theory.

The situation is however totally different as regards the electrocardialogy signal detected within the heart: this signal has an almost constant morphology for each type of cardiac event, the detection being of the point type, that is to say, localised in the region surrounding the sensing electrode itself. It is therefore not possible, in this situation, to rely on morphological analysis for the recognition of ventricular extrasystoles as is done with known external techniques.

However, by utilising both atrial and ventricular sensing, as envisaged in our invention, a ventricular extrasystole is recognised thanks to the fact that this is not preceded by an atrial event but rather by another ventricular event.

The recognition of anomalous ventricular events therefore differs completely according to whether the device utilised for the detection and analysis of the electrocardiologicy signal is outside or inside the human body. It should also be noted that external recording devices can suffer to a very much greater extent than implantable systems from electromagnetic interference, from myopotentials, and from movements of the patient in general. The use of intracardiac electrodes for the detection of the electrical activity of the atrium and of the ventricle represents a guarantee of the correct recording of these events: the reliability of the consequent processing is therefore greater than that carried out by external instruments.

More than this, it should be stressed that the implantable device carries out an analysis of the variability of the heart rate, and hence of the sympatho-vagal balance, continuously, and in real time, the only temporal limit being linked to the exhaustion of its energy supply which happens typically only after several years.

This fact is directly connected to the technology utilised in implantable devices which use highly reliable, low-power circuits.

Even the technological problems are therefore very different from those of external apparatus: for example an electrocardiograph does not have to respect absolute limits of energy consumption and dimensions comparable with those of an implantable object which must necessarily be of small dimensions for the patient and must require an operating energy which is so low that it can operate for several years.

Finally, it is emphasised that the implantable device is able to intervene on the patient at any moment, whenever it is considered necessary, by actuating the therapeutic device associated with the sensing system.

In particular, if a threshold of for example 50 ms and a processing interval of 1 minute are set, a device according to the invention is able to provide, minute by minute, a number of consecutive R-R intervals which differ by at least 50 ms.

It Is moreover possible to set a discrimination threshold in percentage terms with reference to the preceding period, rather than an absolute threshold: for example, it is possible to count, minute by minute, the R-R intervals which differ by more than 6.25% with respect to the preceding R-R interval. This possibility can also, optionally, be rendered programmable. Still by means of programming (according to criteria known per se) it is possible to exclude positive or negative variations of consecutive R-R intervals from the count or to have them both in separate form, independently of the programmed threshold and independently of whether this threshold is of absolute or percentage type.

The possibility of separating the positive variations from the negative variations of the consecutive R-R intervals can be useful in relation to the fact that an increase in the heart rate can be associated directly with a momentary dominance of the sympathetic activity over the vagal activity, whilst a reduction in the heart rate can be associated directly with a momentary dominance of the vagal activity over the sympathetic activity so that the device can be made sensitive only to variations in the sympathetic activity or to those of the regal activity. Moreover, two-chamber sensing constitutes an essential element for any discrimination of anomalous events, permitting correct evaluation of the eympathovagal balance, that is, unaffected by premature heart beats. Finally it is noted that the solution described has no connection with the cardiac acceleration parameter expressed as the maximum acceleration of the spontaneous heart rate, used as a prognostic parameter for the possibility of onset of tachycardia or ventricular fibrillation.

DETAILED DESCRIPTION OF THE INVENTION

The invention will now be described purely by way of non-limitative example with reference to the attached drawings, in which.

Figure 1:
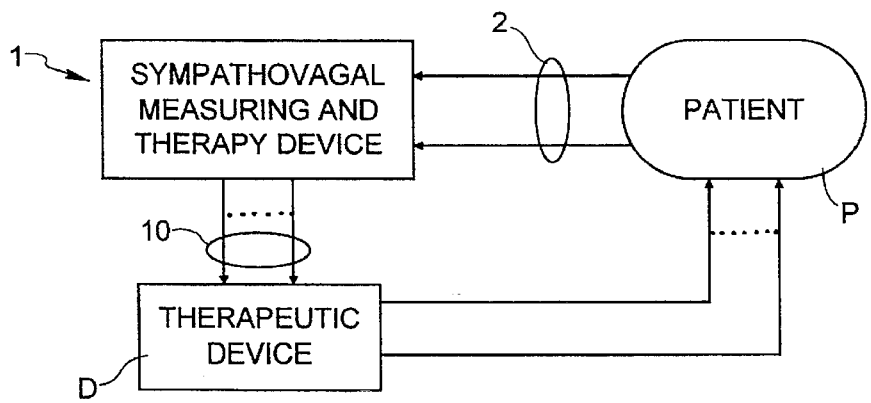
FIG. 1 illustrates in schematic outline the general arrangement of use of a device according to the invention.

In FIG. 1 the reference numeral 1 generally indicates a device for measuring the sympatho-vagal activity which is intended to be implanted in the body of a patient P. The device 1 is intended to operate together with a therapeutic device D, preferably also implantable and, if appropriate, integrated with the device 1 and intended to act on the patient either pharmacologically and/or electrically in dependence on the sympatho-vagal activity measured by the device 1.

As an indication, the device D can, for example, be constituted by a neurological stimulator or by a device for delivering doses of pharmaceuticals such as, for example, the commercial products produced by the United States company Medtronic Inc. of Rice Creek Center 7000, Central Avenue N.E, Minneapolis, USA.

In any case, the characteristics and mode of operation of the device D are considered generally known and therefore not such as to necessitate a detailed description here. Above all, the characteristics of the device D, as well as the manner of association thereof with the body of the patient P, are not relevant to an understanding of the invention.

In general, the device 1 is provided with input terminals 2 on which an electrocardiology signal (ECG) is present.

Figure 2:
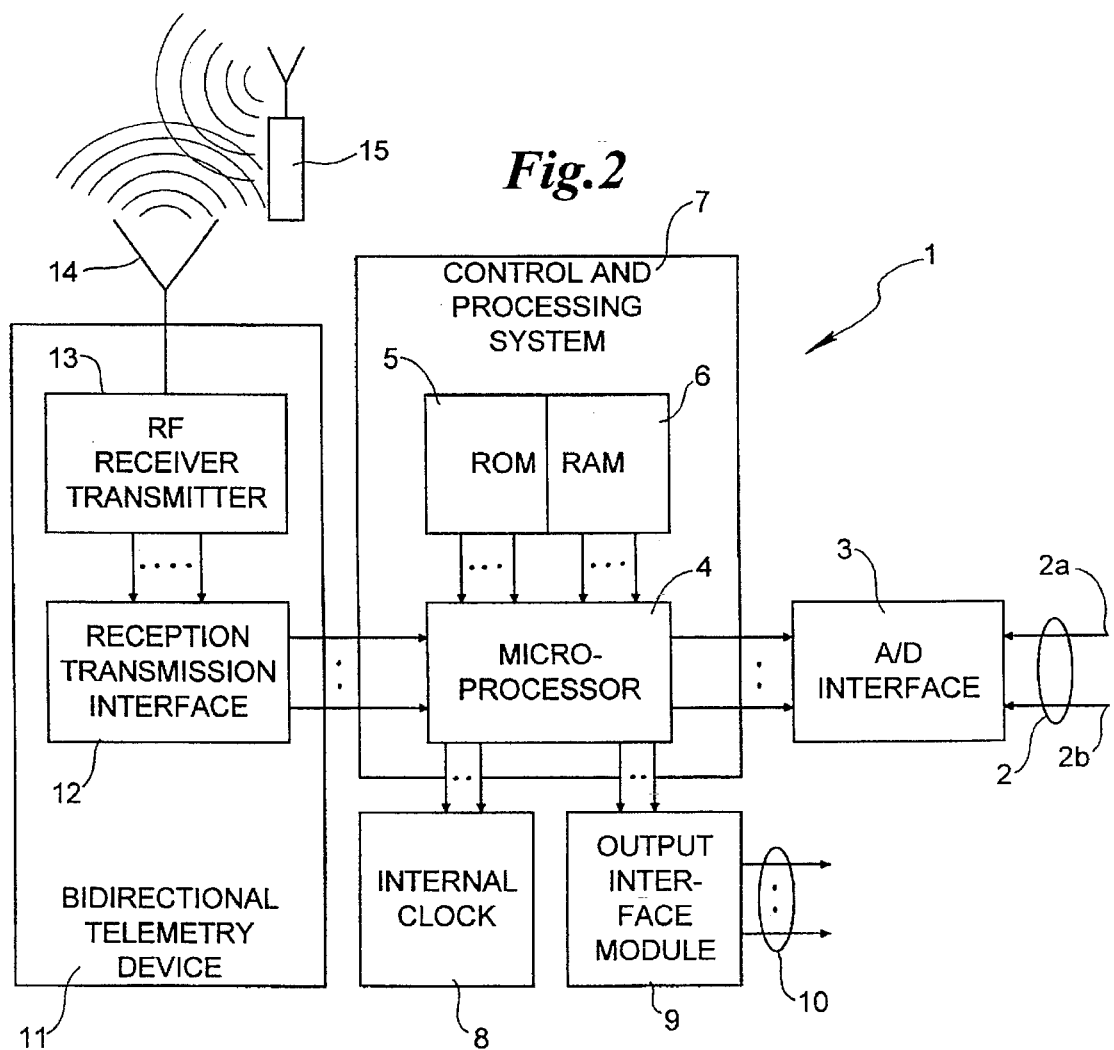
FIG. 2 is a detailed illustration of the internal structure of the device according to the invention in the form of a block circuit diagram.

Preferably (see also the block diagram of FIG. 2) an atrial ECG electrode 2a and a ventricular ECG electrode 2b can be provided, both leading to an analog-to-digital interface 3. The interface 3 transfers the signals provided by the electrodes 2a and 2b, converted into digital form, to the input of a microprocessor 4. This latter, together with respective memories, for example of the ROM 5 and RAM 6 type, forms a control and processing system generally indicated 7 which has an associated internal clock 8 and an output interface module 9 intended to pilot the therapeutic device D via respective output terminals 10.

The reference numeral 11 generally indicates a bi-directional telemetry device comprising a reception/transmission interface 12 connected to the microprocessor 4 as well as a radio-frequency receiver-transmitter 13 connected in bi-directional transmission relationship with the interface 12 leading to a receiver-transmitter aerial 14.

The processing and control circuit 7 supervises all the operating phases of the device and processes the data coming from the adjacent interfaces. To this end, the ROM memory 5 preferably functions as a program memory whilst the RAM memory functions as a processor and store for data programmed and stored by the microprocessor 4 itself in dependence on the processing performed.

The receiver-transmitter 11 (telemetry device) effects an exchange of information between an external programmer device 15 and the control system 7. In particular, it performs the functions of receiving programmed parameters from the outside and transmitting values stored in the RAM memory. Typically, the data transmitted relate to parameters processed by the system after measurement has been effected or after checking for correct dialogue between the external programmer and the implanted device. The transmission and reception of data between the implantable device and the external programmer, am already mentioned, occurs at radio frequency. This is entirely according to technical characteristics well known per se to the man skilled in the art.

The internal clock 8, which is also programmable, is able to provide the processing system with the clock reference essential for an evaluation of a normal measurement of the sympatho-vagal activity.

The analog-to-digital interface 3 is typically provided with atrial and ventricular sensing circuits which are able to recognise the electrical activities of the atrium and of the right ventricle and to discriminate against interference from other sources. The signals representing the information sensed are transmitted in digital form to the processing and control system 7 which utilises them for the purpose of prognosis and/or therapy according to its inherent processing algorithm according to the values of the programmed parameters. This interface therefore puts the sensing catheter or catheters 2a, 2b into communication with the information processing and control device 7. In particular the sensing devices 2a, 2b are made by the same technology as that used in current cardio-electrostimulators for performing the same function. The output interface 9 transmits the intervention command to the therapeutic device D together with the values of the parameters which quantify the magnitude of the evaluated sympatho-vagal imbalance, thus permitting the therapeutic device to operate in an optimal manner.

As a basic consideration it should again be noted that the individual circuits forming the blocks 3 to 15 are individually known per se.

Figure 3:
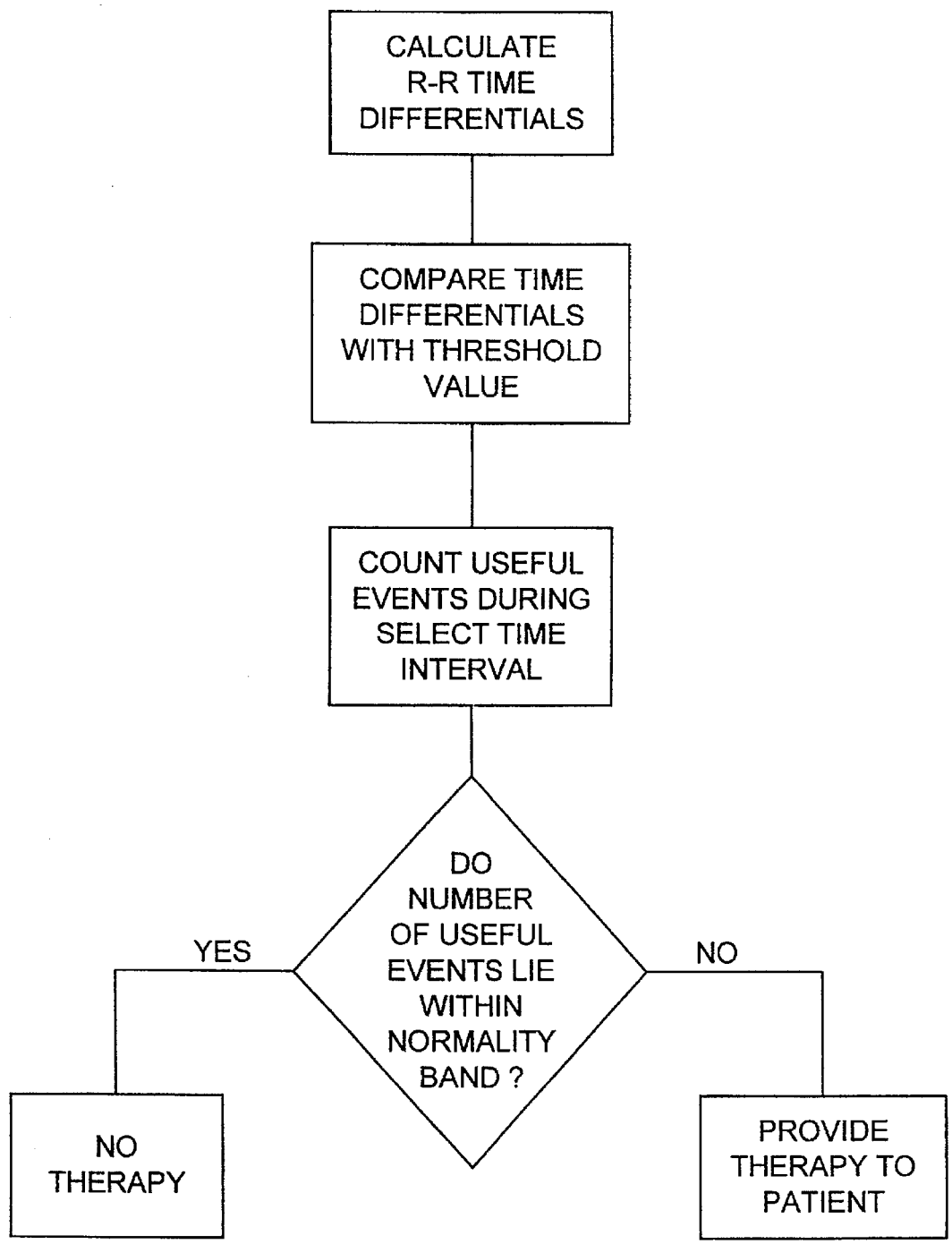
FIG. 3 is a flow chart of the operation of the processing and control system.

In its fundamental aspect the invention is based on criteria adopted for the analysis of electrocardialogy signals picked up through the catheters 2a, 2b. In particular this action can be effected with two individual monopolar or bipolar catheters or with a single catheter which could be provided with two or four electrodes respectively, intended in each case to be located close to the atrium and to the right ventricle. The knowledge both of the atrial signal and of the ventricular signal allows the system to discriminate between the instantaneous sinusal heart rate and momentary, spurious frequencies which can result from the presence of arrythmia. The signal thus discriminated is sent to the processing and control system 7 which processes the signal in accordance with the flow chart in FIG. 3. The processing and control system 7 calculates the difference between the current R-R period and the preceding one and compares the result with a programmable threshold, typically of 50 ms. The events which exceed this value, defined as useful events, are counted, the count interval being programmable in discrete steps from a minimum of one minute to a maximum of one hour. The purpose of the system being to provide a signal which triggers a therapeutic device, particular attention must be given to the intervention criteria, For this purpose a normality band is defined within which the number of useful events counted must lie: this will vary over a 24 hour period in that the sympatho-vagal balance assumes different physiological values during the course of a day. In particular, during nocturnal hours, the vagal system typically dominates whilst, during the day, the sympathetic system typically dominates. The normality band has an upper limit linked to the maximum acceptable imbalance in favour of the vagal system whilst its lower limit corresponds to the maximum acceptable imbalance in favour of the sympathetic system. Consequently, the system includes the internal clock 8 which is programmable so as to associate the correct normality band, and consequently the correct intervention values, with each phase of the day. The possibility of telemetric communication of this data enables the optimum intervention conditions, which have to be personalised to the patient, to be evaluated in vivo. If it is found that the upper or lower limit of the normality band for the current hour is exceeded, the system enables the starting of the therapeutic procedure (the nature of which, as mentioned, does not constitute the subject of the present invention but may in any case be of pharmacological and/or electrical type).

In each case, the therapeutic intervention device will receive both the data relating to the type of imbalance, that is, whether it favours the vagal or the sympathetic system, and a quantitative evaluation of the change: the therapeutic action may thus be metered according to the magnitude and type of sympatho-vagal imbalance.

In particular, as already indicated above, by means of the microprocessor 4 it is possible to set a discrimination threshold in percentage terms with reference to a preceding period rather than an absolute threshold: for example, it is impossible to count, minute by minute, the R-R intervals which differ by more than 6.25% from the preceding R-R intervals. This possibility can also, optionally, be made programmable. Again by programming of the microprocessor 4, it is possible to exclude either the positive or the negative variations of consecutive R-R intervals from the count or to have them both in separate form, whatever the programmed threshold and independently of whether this threshold is of the absolute or of the percentage type, so as to separate the positive variations of consecutive R-R intervals from the negative variations.

The modes of operation and criteria which can be adopted for the programming of the microprocessor 4 to achieve the aforesaid objects are widely known to those skilled in the art and do not, therefore, need to be described herein.

What is claimed is:

1. A method of providing therapy to a patient comprising:
   implanting at least one sensor in the proximity of the patient's heart;
   sensing the electrical activity of the patient's heart from the at least one sensor;
   generating an electrocardiology signal from the sensed electrical activity of the patient's heart;
   repeatedly calculating from the signal a time differential between consecutive R-R intervals;

comparing the time differentials with a predetermined time differential threshold value;

counting the number of time differentials which exceed the predetermined time differential threshold value during a predetermined time interval, that number being equal to the number of useful events;

determining whether the number of useful events lies within a predetermined band of normal values; and providing therapy to the patient if the number of useful events does not lie within the predetermined band of normal values.

2. The method of claim 1 wherein the step of providing therapy comprises delivery of a pharmaceutical agent to the patient.

3. The method of claim 1 wherein the step of providing therapy comprises delivering electrical stimulation to the patient.

4. The method of claim 1 wherein the step of comparing is performed in a programmable control and processing system, the method further comprising programming the control and processing system with the predetermined threshold value.

5. The method of claim 4 further comprising programming the predetermined threshold value to approximately 50 ms.

6. The method of claim 4 further comprising programming the predetermined threshold value as a percentage by which consecutive R-R intervals differ.

7. The method of claim 1 wherein the step of counting is performed in a programmable control and processing system, the method further comprising programming the control and processing system with the predetermined time interval.

8. The method of claim 7 further comprising programming the predetermined time interval in the range of from approximately one minute to one hour.

9. The method of claim 1 further comprising using the results of the calculating, comparing, counting and determining steps to generate a second signal indicative of sympatho-vagal activity and transmitting the second signal to a receiver.

10. The method of claim 1 wherein the step of determining is performed in a programmable control and processing system, the method further comprising programming the control and processing system with the predetermined band of normal values.

11. The method of claim 10 further comprising programming the control and, processing system with a predetermined band of normal values which vary depending on the time of day.

12. The method of claim 1 wherein the sensing step includes sensing electrical activity of the atrium and sensing electrical activity of the ventricle.

13. The method of claim 12 further comprising discriminating from the electrocardiology signal ventricular extrasystoles.

14. The method of claim 1 further comprising discriminating from the electrocardiology signal ventricular extrasystoles.

15. The method of claim 1 wherein the comparing step includes differentiating between positive time differentials and negative time differentials and wherein the counting step includes counting only positive time differentials.

16. The method of claim 1 wherein the comparing step includes differentiating between positive time differentials and negative time differentials and wherein the counting step includes counting only negative time, differentials.

17. The method of claim 1 wherein the comparing step includes differentiating between positive time differentials and negative time differentials and wherein the counting step includes separately counting negative time differentials and positive time differentials.

18. A device for providing therapy to a patient comprising:

means for implantation within the patient for sensing the electrical activity of the patient's heart;

means for generating an electrocardiology signal from the sensed electrical activity of the patient's heart;

means for repeatedly calculating from the signal a time differential between consecutive R-R intervals;

means for comparing the time differentials with a predetermined time differential threshold value;

means for counting the number of time differentials which exceed the predetermined time differential threshold value during a predetermined time interval, that number being equal to the number of useful events;

means for determining whether the number of useful events lies within a predetermined band of normal values; and means for providing therapy to the patient if the number of useful events does not lie within the predetermined band of normal values.

19. The device of claim 18 wherein the means for calculating, comparing, counting, determining and providing therapy are contained within at least one assembly which is sized to be implanted in the body of the patient.

20. The device of claim 19 wherein the means for sensing, calculating, comparing, counting and determining are integrated within a single implantable assembly.

21. The device of claim 18 wherein the means for comparing is adapted to be programmed with the predetermined threshold value.

22. The device of claim 21 wherein the predetermined threshold value is approximately 50 ms.

23. The device of claim 21 wherein the predetermined threshold value is a percentage by which consecutive R-R intervals differ.

24. The device of claim 23 wherein the percentage is 6.25 percent.

25. The device of claim 18 wherein the means for counting is adapted to be programmed with the predetermined time interval.

26. The device of claim 25 wherein the length of the predetermined time interval is in the range of from approximately one minute to one hour.

27. The device of claim 18 further including means responsive to the calculating, comparing, counting and determining means for generating a second signal indicative of sympatho-vagal activity and means for transmitting the second signal to a receiver.

28. The device of claim 18 wherein the means for determining is adapted to be programmed with the predetermined band of normal values.

29. The device of claim 28 further including means for selectively varying the predetermined band of normal values depending on the time of day.

30. The device of claim 18 wherein the sensing means includes means for sensing electrical activity in the atrium and means for sensing electrical activity in the ventricle.

31. The device of claim 30 further comprising means for discriminating from the electrocardiology signal ventricular extrasystoles.

32. The device of claim 18 further comprising means for discriminating from the electrocardiology signal ventricular extrasystoles.

33. The device of claim 18 wherein the comparing means includes means for differentiating between positive time differentials and negative time differentials and wherein the counting means includes means for counting only positive time differentials.

34. The device of claim 18 wherein the comparing means includes means for differentiating between positive time differentials and negative time differentials and wherein the counting means includes means for counting only negative time differentials.

35. The device of claim 18 wherein the comparing means includes means for differentiating between positive time differentials and negative time differentials and wherein the counting means includes means for separately counting negative time differentials and positive time differentials.

36. A device for providing therapy to a patient comprising:

at least one sensor sized for implantation within the patient having an output indicative of the electrical activity of the patient's heart;

a signal generator connected to receive the output of the at least one sensor and responsive thereto to generate an electrocardiology signal;

a processor connected to receive the cardiology signal and to:

a) repeatedly calculate from the signal a time differential between consecutive R-R intervals;

b) compare the time-differentials with a predetermined time differential threshold value;

c) count the number of time differentials which exceed the predetermined time differential threshold value during a predetermined time interval, that number being equal to the number of useful events; and d) determine whether the number of useful events lies within a predetermined band of normal values;

the processor producing an output signal indicative of the sympatho-vagal activity of the patient's heart; and a therapy dispenser responsive to the processor output signal to dispense therapy to the patient if the number of useful events does not lie within the predetermined band of normal values.

37. The device of claim 36 wherein the processor and the therapy dispenser are contained within at least one assembly sized to be implanted in the body of the patient.

38. The device of claim 37 wherein the processor is integrated within a single implantable assembly.

39. The device of claim 36 wherein the processor is adapted to be programmed with the predetermined threshold value.

40. The device of claim 39 wherein the predetermined threshold value is approximately 50 ms.

41. The device of claim 39 wherein the predetermined threshold value is a percentage by which consecutive R-R intervals differ.

42. The device of claim 41 wherein the percentage is 6.25 percent.

43. The device of claim 36 wherein the processor is adapted to be programmed with the predetermined time interval.

44. The device of claim 43 wherein the length of the predetermined time interval is in the range of from approximately one minute to one hour.

45. The device of claim 36 further including a transmitter and a receiver, the transmitter being operative to transmit the output signal of the processor to the receiver.

46. The device of claim 36 wherein the processor is adapted to be programmed with the predetermined band of normal values.

47. The device of claim 46 wherein the predetermined band of normal values is programmed to vary depending on the time of day.

48. The device of claim 36 wherein the at least one sensor includes a sensor for sensing electrical activity in the atrium and a sensor for sensing electrical activity in the ventricle.

49. The device of claim 48 wherein the signal generator discriminates ventricular extrasystoles from the electrocardiology signal.

50. The device of claim 36 wherein the signal generator discriminates ventricular extrasystoles from the electrocardiology signal.

51. The device of claim 36 wherein the processor differentiates between positive time differentials and negative time differentials and counts only positive time differentials.

52. The device of claim 36 wherein the processor differentiates between positive time differentials and negative time differentials and counts only negative time differentials.

53. The device of claim 36 wherein the processor differentiates between positive time differentials and negative time differentials and separately counts negative time differentials and positive time differentials.

* * * * *

UNITED STATES PATENT AND TRADEMARK OFFICE
CERTIFICATE OF CORRECTION

PATENT NO. : 5,645,570
DATED : July 8, 1997
INVENTOR(S) : Giorgio Corbucci

It is certified that error appears in the above-identified patent and that said Letters Patent is hereby corrected as shown below:

Column 1, line 58, replace "dotion" with --action--.
Column 3, line 31, replace "regal" with --vagal--; line 39, replace "utllised" with --utilised--.
Column 4, line 1, replace "With" with --with--; line 54, replace "Molter" with --Holter--.
Column 6, line 10, replace "regal" with --vagal--; line 12, replace "eympatho-" with --sympatho- --.
Column 7, line 24, replace "am" with --as--.
Column 8, line 9, replace "criteria," with --criteria.--.
Claim 11, line 2, delete ",".
Claim 16, line 4, delete ",".
Claim 36, line 13, delete "-".

Signed and Sealed this

Eighteenth Day of April, 2000

Attest:

Q. TODD DICKINSON

*Attesting Officer*    *Director of Patents and Trademarks*